United States Patent [19]
Vehige et al.

[11] Patent Number: 5,858,346
[45] Date of Patent: Jan. 12, 1999

[54] COMPOSITIONS AND METHODS FOR ENHANCING CONTACT LENS WEARABILITY

[75] Inventors: Joseph G. Vehige, Laguna Niguel; James P. Currie, Trabuco Canyon, both of Calif.

[73] Assignee: Allergan, Waco, Tex.

[21] Appl. No.: 854,221

[22] Filed: May 9, 1997

[51] Int. Cl.⁶ .............................. A61L 2/18; A61K 31/74
[52] U.S. Cl. ........................................ 424/78.04; 514/840
[58] Field of Search ........................... 424/78.04; 514/840

[56] References Cited

U.S. PATENT DOCUMENTS

| | | |
|---|---|---|
| 3,549,747 | 12/1970 | Krezanoski et al. |
| 4,029,817 | 6/1977 | Blanco et al. |
| 4,436,730 | 3/1984 | Ellis et al. |
| 4,615,882 | 10/1986 | Stockel |
| 4,786,436 | 11/1988 | Ogunbiyi et al. |
| 4,836,986 | 6/1989 | Ogunibiyi et al. ................ 424/78.04 |
| 5,356,555 | 10/1994 | Huth et al. |
| 5,424,078 | 6/1995 | Dziabo et al. |
| 5,593,637 | 1/1997 | Mowrey-McKee et al. |

*Primary Examiner*—Peter F. Kulkosky
*Attorney, Agent, or Firm*—Frank J. Uxa

[57] ABSTRACT

Compositions and methods for treating a contact lens very effectively and conveniently provide enhanced contact lens wearability by reducing the actual or perceived ocular sensitivity which results from exposing a contact lens to non-oxidative antimicrobial components. The present system takes advantage of inactivating or deactivating a non-oxidative antimicrobial component located on or in a contact lens to reduce the ocular sensitivity caused by placing the lens in the eye.

12 Claims, No Drawings

COMPOSITIONS AND METHODS FOR ENHANCING CONTACT LENS WEARABILITY

BACKGROUND OF THE INVENTION

This invention relates to compositions and methods useful for enhancing the wearability of contact lenses. More particularly, the invention relates to compositions and methods in which contact lenses on or in which are located non-oxidative antimicrobial components are treated to inactivate such antimicrobial components.

Various compositions, such as solutions, are used in association with contact lenses to ensure that the lenses may be safely, comfortably and conveniently worn. Contact lens care compositions often utilize at least one antimicrobial component, for example, for disinfecting contact lenses after wear.

A contact lens disinfecting composition generally has sufficient antimicrobial activity so that when the composition is contacted with a contact lens to be disinfected, microorganisms associated with the lens are killed or otherwise removed and the contact lens is effectively disinfected within a reasonable time, for example, in the range of about 0.1 hour to about 12 hours. A contact lens disinfecting composition may be termed a microbicidal composition. In contrast, a preserved contact lens care composition has sufficient antimicrobial activity, often less of such activity than is present in a contact lens disinfecting composition, so that when the composition is contacted with a contact lens substantially no increase in the microorganism population on the lens or in the composition is obtained. A preserved contact lens care composition may be termed a microbiostatic composition.

Non-oxidative antimicrobial components have been suggested for use in disinfecting contact lens. One advantage of such non-oxidative materials is that they lend themselves quite well to a one step approach to disinfecting contact lens. For example, the non-oxidative antimicrobial component can be included in a multi-purpose contact lens care solution which is used to disinfect the lens. The disinfected lens is then taken directly from the solution and placed in the eye. No rinsing or other processing is required. As the name implies, such multi-purpose solutions can be used for purposes other than disinfecting contact lenses, such as rinsing, storing and rewetting contact lenses.

Although this approach to contact lens care has proven to be quite effective and very convenient, some degree of ocular sensitivity to non-oxidative antimicrobial components has been experienced, or at least perceived, by contact lens wearers. Even when such non-oxidative materials are used as preservatives, some degree of actual or perceived ocular sensitivity may occur. Such non-oxidative antimicrobial components tend to accumulate on or in contact lenses over time (and repeated treatments with multi-purpose solutions), resulting in increased ocular sensitivity.

It would be advantageous to provide a contact lens care system in which the ocular sensitivity to non-oxidative antimicrobial components is reduced or even eliminated and contact lens wearability is enhanced.

SUMMARY OF THE INVENTION

New compositions and methods for enhancing the wearability of a contact lens on or in which is located a non-oxidative antimicrobial component have been discovered. The present compositions and methods very effectively and conveniently provide enhanced contact lens wearability by reducing the actual or perceived ocular sensitivity which results from exposing a contact lens to non-oxidative antimicrobial components, such as non-oxidative disinfectant components and non-oxidative preservative components and the like. The present systems, that is the present compositions and methods, take advantage of inactivating or deactivating a non-oxidative antimicrobial component located on or in a disinfected contact lens to reduce the ocular sensitivity after the lens is placed in the eye. Since, in one embodiment, the antimicrobial component is inactivated before the lens is placed in the eye, higher potency antimicrobial components and/or high concentrations of antimicrobial components can be used (relative to what is conventionally used), for example, which can result in more effective and/or rapid contact lens disinfection. These advantages are achieved while, at the same time, reducing or eliminating ocular sensitivity caused by the presence of active antimicrobial component in the eye.

In one broad aspect of the present invention, methods for enhancing the wearability of a contact lens are provided which comprise contacting a contact lens, for example, a disinfected contact lens, on or in which is located a non-oxidative antimicrobial component with a defined aqueous liquid medium. This aqueous liquid medium contains an effective amount of an inactivating component, hereinafter referred to as an IC, at conditions effective to inactivate the non-oxidative antimicrobial component located on or in the contact lens. Thus, before the disinfected lens is placed in the eye for wear, the non-oxidative antimicrobial component located on or in the lens is inactivated. The contact lens is then placed in the eye, preferably directly from the IC contacting step. Since the non-oxidative antimicrobial component is inactivated, the eye's sensitivity to the antimicrobial component is reduced, or even eliminated, and the wearability of the lens is enhanced.

In a particularly useful embodiment, the contact lens is a hydrophilic contact lens and at least a portion of the non-oxidative antimicrobial component is sorbed in or on the hydrophilic contact lens before the IC contacting step.

As noted above, the contact lens contacted with the IC may be a disinfected contact lens. Thus, in one embodiment, the present methods preferably further comprise contacting the contact lens with a liquid material including an effective disinfecting amount of a non-oxidative antimicrobial component at conditions effective to disinfect the contact lens. This non-oxidative antimicrobial component contacting step preferably is performed prior to the contacting with the IC.

The aqueous liquid medium including the IC preferably is free of the non-oxidative antimicrobial component prior to being contacted with the contact lens. The IC advantageously is present in an amount effective to inactivate all the non-oxidative antimicrobial component located on or in the contact lens.

The IC preferably is selected from polyanionic components and mixtures thereof. A very useful group of ICs include polymeric materials having multiple anionic charges and mixtures thereof.

The use of polyanionic ICs is particularly advantageous when the non-oxidative antimicrobial component located on or in the contact lens is selected from cationic, such as polycationic, antimicrobial components and mixtures thereof.

In another broad aspect of the present invention, compositions for enhancing the wearability of a contact lens are provided. Such compositions comprise an aqueous liquid medium; an IC, e.g., as described elsewhere herein, soluble in the aqueous liquid medium and present in an amount effective to inactivate a non-oxidative antimicrobial component located on or in a contact lens contacted with the composition; and, optionally, a preservative component in amount effective to preserve the composition. Of course, the preserving activity of the preservative component should be effective in the presence of the IC. Preferably, the preservative component has a reduced propensity to cause discomfort or sensitivity in a human eye relative to the non-oxidative antimicrobial component located on or in a contact lens contacted with the composition. In a particularly useful embodiment, the preservative component is selected from the group consisting of chlorine dioxide precursors and mixtures thereof, more preferably one or more chlorites and/or stabilized chloride dioxide.

The compositions described immediately above are preferably packaged in bulk or multi-dose quantities of about 5 ml or about 10 ml to about 150 ml or about 500 ml. In such multi-dose quantities, the preservative is effective to maintain the remaining composition effectively microbiostatic between uses.

In another broad aspect of the present invention, compositions for enhancing the wearability of a contact lens are provided and are of particular applicability in situations where no preservative is required. Such compositions may be provided in single dose quantities, for example, in a sealed package the contents of which are consumed in a single use, for example, treating two (2) contact lenses, after the package is opened. Preferably these compositions are packaged so that separate individual amounts in the range of about 0.2 ml to about 20 ml are provided.

Such compositions comprise an aqueous liquid medium and an IC, e.g., as described elsewhere herein, soluble is the aqueous liquid medium and present in an amount effective to inactivate an non-oxidative antimicrobial component located on or in a contact lens contacted with the composition. Such compositions are free of preservatives.

In a very useful embodiment, the present compositions further include a scavenger component present in an amount effective to inactivate a sequestering or chelating component located on or in a contact lens contacted with the composition. Preferably, the scavenger component is ophthalmically acceptable and is selected from calcium salts, magnesium salts and mixtures thereof.

These and other aspects and advantages of the present invention are apparent in the following detailed description, examples and claims.

DETAILED DESCRIPTION OF THE INVENTION

The present invention is useful for treating, for example, rubbing, rinsing, soaking, wetting, conditioning and the like, contact lenses to enhance the wearability of such lenses. Any contact lens, for example, conventional hard contact lenses, rigid gas permeable contact lenses and soft contact lenses, can be treated in accordance with the present invention. However, the present invention is particularly applicable for use with soft, hydrophilic contact lenses, that is soft contact lenses which have equilibrium water contents of at least about 30% or about 35%, for example, about 38% to about 78% or more, by weight.

In one aspect, the present compositions for enhancing the wearability of a contact lens comprise an aqueous liquid medium, and an IC soluble in the aqueous liquid medium and present in an amount effective to inactivate a non-oxidative antimicrobial component located on or in a contact lens contacted with the composition. The IC preferably is ophthalmically acceptable in the aqueous liquid medium. The compositions can be substantially free of antimicrobial components, for example, non-oxidative antimicrobial components.

In one useful embodiment, the present compositions are free of preservatives. Such preservative-free compositions preferably are packaged in separate single dose quantities, more preferably in the range of about one 0.2 ml to about 20 ml per single dose, which are completely consumed in a single use treating up to two (2) contact lenses. Using such preservative-free compositions further enhances the wearability of the treated contact lens, for example, since any ocular sensitivity caused by the presence of preservative components is eliminated.

In another useful embodiment, the present compositions further comprise preservative components in amounts effective to preserve the compositions. The preservative activity of the preservative components is effective in the presence of the IC. Particularly useful preservative components include those having a reduced propensity to cause discomfort in a human eye relative to the non-oxidative antimicrobial component located on or in a contact lens contacted with the composition. The inclusion of a preservative component allows the present compositions to more effectively be packaged in multi-dose quantities, for example, on the order of about 5 ml or about 10 ml or about 150 ml to about 500 ml. The use of preservative components having a reduced propensity to cause ocular discomfort, as described above, allows substantial additional benefits to be obtained.

The present compositions can be initially contacted with the contact lens outside the eye or while the lens is being worn in the eye. Beside inactivating the non-oxidative antimicrobial component in or on the contact lens, the present compositions may be employed to pre-wet and/or rewet the lens, condition the lens, lubricate the lens and/or otherwise benefit the lens in or out of the eye.

A liquid aqueous medium or other material is "ophthalmically acceptable" when it is compatible with ocular tissue, that is, it does not cause significant or undue detrimental effects when brought into contact with ocular tissue. Preferably, the ophthalmically acceptable material is also compatible with other components of the present compositions.

Any material or combination of materials may be used as an IC in accordance with the present invention provided that it functions as described herein and has no undue detrimental effect on the contact lens being treated or on the wearer of the treated contact lens. The IC itself preferably is ophthalmically acceptable. The IC preferably interacts with the non-oxidative antimicrobial component located on or in the contact lens rapidly to inactivate, more preferably essentially irreversibly inactivate, the antimicrobial component. In the event the inactivation results in the formation of one or more other substances, preferably such other substances are ophthalmically acceptable.

Preferred ICs for use in the present invention include polyanionic components and the like and mixtures thereof.

As used herein, the term "polyanionic component" refers to a chemical entity, for example, an ionically charged species, such as an ionically charged polymeric material, which includes more than one discrete anionic charge, that is multiple discrete anionic charges. The polyanionic component is selected to be "compatible" with or effective to inactivate the particular non-oxidative antimicrobial component involved or of interest. Thus, the IC is polyanionic relative to the specific non-oxidative antimicrobial component to be inactivated. Preferably, the polyanionic component is selected from the group consisting of polymeric materials having multiple anionic charges and mixtures thereof.

The IC, for example, polyanionic component, is effective, for example, is sufficiently anionic and is present in sufficient concentration, to render the non-oxidative antimicrobial component on or in the contact lens inactive, for example, to interact with the non-oxidative antimicrobial component, which preferably is cationically charged. This interaction is sufficient to render the non-oxidative disinfectant component inactive, and preferably irreversibly deactivated.

Any suitable polyanionic component may be employed in accordance with the present invention provided that it functions as described herein and has no substantial detrimental effect on the contact lens or on the wearer of the contact lens. The polyanionic component is preferably ophthalmically acceptable at the concentrations used. The polyanionic component preferably includes three (3) or more anionic (or negative) charges. In the event that the polyanionic component is a polymeric material, it is preferred that each of the repeating units of the polymeric material include a discrete anionic charge. Particularly useful anionic components are those which are water soluble, for example, soluble at the concentrations used in the presently useful aqueous liquid media.

Examples of suitable polyanionic components useful as ICs in the present invention include anionic cellulose derivatives, anionic acrylic acid-containing polymers, anionic methacrylic acid-containing polymers, anionic amino acid-containing polymers and mixtures thereof. Anionic cellulose derivatives are very useful in the present invention.

A particularly useful class of polyanionic components are one or more polymeric materials having multiple anionic charges. Examples include:
    metal carboxymethylcelluloses
    metal carboxymethylhydroxyethylcelluloses
    metal carboxymethylstarchs
    metal carboxymethylhydroxyethylstarchs
    hydrolyzed polyacrylamides and polyacrylonitriles
    heparin
    gucoaminoglycans
    hyaluronic acid
    chondroitin sulfate
    dermatan sulfate
    peptides and polypeptides
    alginic acid
    metal alginates
    homopolymers and copolymers of one or more of:
        acrylic and methacrylic acids
        metal acrylates and methacrylates
        vinylsulfonic acid
        metal vinylsulfonate
        amino acids, such as aspartic acid, glutamic acid and the like
        metal salts of amino acids
        p-styrenesulfonic acid
        metal p-styrenesulfonate
        2-methacryloyloxyethylsulfonic acids
        metal 2-methacryloyloxethylsulfonates
        3-methacryloyloxy-2-hydroxypropylsulonic acids
        metal 3-methacryloyloxy-2-hydroxypropylsulfonates
        2-acrylamido-2-methylpropanesulfonic acids
        metal 2-acrylamido-2-methylpropanesulfonates
        allylsulfonic acid
        metal allylsulfonate and the like.

Excellent results are achieved using ICs selected from carboxymethylcelluloses and mixture thereof, for example, alkali metal and/or alkaline earth metal carboxymethylcelluloses. In one embodiment, the IC is other than carboxymethylcelluloses and mixtures thereof. Thus, compositions which include ICs and are free of carboxymethylcellulose, for example, sodium carboxymethylcellulose, are included within the scope of the present invention.

The amount of IC employed is that effective to inactivate the non-oxidative antimicrobial component located on or in the contact lens contacted with the present composition. The specific amount of such component used is not critical to the present invention provided that it functions as an IC, as described herein. In addition, the amount of IC employed depends on a number of factors, for example, the specific IC being employed, the concentration or amount of non-oxidative antimicrobial component present and the degree of non-oxidative antimicrobial component inactivation desired. Also, the amount of IC used may take into account one or more other benefits obtained from the presence of the IC. For example, the IC may be effective to provide beneficial viscosity and/or lubricating enhancements if employed in the proper concentrations. It is preferred that the amount of IC employed be effective to inactivate the non-oxidative antimicrobial component and provide one or more other benefits to the contact lens being treated and/or to the wearer of the treated contact lens. Further, the amount of IC preferably is controlled so that there is little or no carry over of the IC on the lens at the conclusion of the period of lens wear. Such carry over can have a detrimental effect on the ability to disinfect the lens after such period of wear. Preferably, the IC is present in an amount of about 0.01% or about 0.05% (w/v) to about 1% or about 2% or about 5% (w/v).

The concentration of the IC in the present compositions may be varied depending on the amount of the composition used per lens treatment. For example, if the amount of composition used per lens treatment is less than 5 ml and/or the composition is packaged in single dose or use units, the concentration of the IC preferably is relatively high so that the relatively small amount of composition includes sufficient IC to effectively inactivate the non-oxidative antimicrobial component located in or on the contact lens. Conversely, if the amount of composition used per lens treatment is 5 ml or more and/or the composition is packaged in bulk or multi-dose quantative, the concentration of the IC can be relatively low provided that sufficient IC is present during the lens treating to effectively inactivate the non-oxidative antimicrobial component located in or on the lens or lenses being treated.

As used herein, substantially non-oxidative antimicrobial components include effectively non-oxidative organic chemicals which derive their antimicrobial activity through a chemical or physiochemical interaction with the microbes or microorganisms. Suitable such non-oxidative components comprise those generally employed in ophthalmic applications and include, but are not limited to, quaternary ammonium salts used in ophthalmic applications such as poly [dimethylimino-2-butene-1,4-diyl]chloride, alpha-[4-tris(2-hydroxyethyl) ammonium]-dichloride (chemical registry number 75345-27-6, available under the trademark Polyquarternium 1® from Onyx Corporation), benzalkonium halides, and biguanides such as salts of alexidine, alexidine-free base, salts of chlorhexidine, hexamethylene biguanides and their polymers, antimicrobial polypeptides, and the like and mixtures thereof. A particularly useful substantially non-oxidative component is selected from tromethamine (2-amino-2-dydroxymethyl-1, 3 propanediol) and its ophthalmically acceptable salts in combination with a microbicide component selected from polyhexamethylene biguanide (PHMB), N-alkyl-2-pyrosolidone, chlorhexidine, Polyquarternium-1, hexetidine, bronopol, alexidine, ophthalmically acceptable salts thereof and mixtures thereof.

The salts of alexidine and chlorhexidine can be either organic or inorganic and are typically gluconates, nitrates, acetates, phosphates, sulphates, halides and the like. Generally, the hexamethylene biguanide polymers (PHMB), also referred to as polyaminopropyl biguanide (PAPB), have molecular weights of up to about 100,000. Such compounds are known and are disclosed in U.S. Pat. No. 4,758,595.

When a contact lens is desired to be disinfected by a disinfectant component, an amount of disinfectant effective to disinfect the lens is used. Preferably, such an effective amount of the disinfectant reduces the microbial burden on the contact lens by one log order, in three hours. More preferably, an effective amount of the disinfectant reduces the microbial load by one log order in one hour.

The disinfectant component in accordance with the present invention is preferably provided in the aqueous liquid medium, and is more preferably soluble in the aqueous liquid medium. The substantially non-oxidative disinfectant components useful in the present invention preferably are present in the aqueous liquid medium in concentrations in the range of about 0.00001% to about 2% (w/v).

A suitable preservative component may be included in the present compositions provided that such components is effective as a preservative in the presence of the IC. Thus, it is important that the preservative component be substantially unaffected by the presence of the IC. For example, if the IC is, as is preferred, a polyanionic component, the preservative component is unaffected by the polyanionic component. Of course, the preservative component chosen depends on various factors, for example, the specific IC present, the other components present in the composition, etc. Examples of the useful preservative components include, but are not limited to, per-salts, such as perborates, percarbonates and the like; peroxides, such as very low concentrations, e.g., about 50 to about 200 ppm (w/v), of hydrogen peroxide and the like; alcohols, such as benzyl alcohol, chlorbutanol and like; sorbic acid and ophthalmically acceptable salts thereof and mixtures thereof.

The amount of preservative component included in the present compositions containing such a component varies over a relatively wide range depending, for example, on the specific preservative component employed. The amount of such component preferably is in the range of about 0.000001% to about 0.05% or more (w/v) of the present composition.

In a very useful embodiment, the preservative component has a reduced propensity to cause discomfort, for example, ocular sensitivity, irritation and the like, in the human eye relative to the non-oxidative disinfectant component located on or in a contact lens contacted with the preservative component-containing composition. This "reduced propensity" feature of the present invention may be obtained simply because the amount or concentration of the preservative component in the present compositions is often less than the amount or concentration of the disinfectant component present in the disinfecting aqueous liquid medium.

Although such "reduced concentrations" embodiment is beneficial and is within the scope of the present invention, it is more preferred that the preservative component employed in the present compositions have an inherently reduced propensity to cause discomfort in a human eye relative to the non-oxidative disinfectant component located on or in a contact lens contacted with the composition. In other words, more preferably the preservative component at the concentration in the present composition has such a "reduced propensity" relative to the non-oxidative disinfectant component present in the same concentration.

One particularly useful class of "reduced propensity" preservative components are chlorine dioxide precursors. Specific examples of chlorine dioxide precursors include stabilized chlorine dioxide (SCD), metal chlorites, such as alkali metal and alkaline earth metal chlorites, and the like and mixtures thereof. Technical grade sodium chlorite is a very useful chlorine dioxide precursor. Chlorine dioxide-containing complexes, such as complexes of chlorine dioxide with carbonate, chlorine dioxide with bicarbonate and mixtures thereof are also included as chlorine dioxide precursors. The exact chemical composition of many chlorine dioxide precursors, for example, SCD and the chlorine dioxide complexes, is not completely understood. The manufacture or production of certain chlorine dioxide precursors is described in McNicholas U.S. Pat. No. 3,278,447, which is incorporated in its entirety herein by reference. Specific examples of useful SCD products include that sold under the trademark Dura Klor by Rio Linda Chemical Company, Inc., and that sold under the trademark Anthium Dioxide by International Dioxide, Inc.

The chlorine dioxide precursor is included in the present compositions to effectively preserve the compositions. Such effective preserving concentrations preferably are in the range of about 0.0002 or about 0.002 to about 0.02% (w/v) of the present compositions.

In the event that chlorine dioxide precursors are employed as preservative components, the compositions preferably have an osmolality of at least about 200 mOsmol/kg and are buffered to maintain the pH within an acceptable physiological range, for example, a range of about 6 to about 10.

Quite often the disinfectant-containing composition includes a chelating or sequestering component in an amount effective to provide at least one beneficial properties to the composition. For example, such chelating components is often effective to enhance the antimicrobial activity of the composition and/or to prevent deposition of microbial residues, minerals, and other debris in the composition on the contact lens being disinfected.

Examples of useful chelating components include disodium ethylene diamine tetraacetate (EDTA), alkali metal hexametaphosphate, citric acid, sodium citrate, and the like and mixtures thereof. Such chelating components preferably are present in the amount in the range of about 0.01 to about 1% (w/v) of the disinfectant-containing composition.

In order to ensure the effectiveness of such chelating components, excess amounts are often used. Thus, after the disinfecting contacting, the active chelating component is located in or on the disinfected contact lens. Such active chelating agent can cause ocular sensitivity and/or one or more other detrimental effects to the eye in which the disinfected lens is placed.

The present compositions preferably include an effective amount of a scavenger component effective to interact with the chelating component located in or on the disinfectant contact lens to render such chelating component inactive, and preferably substantially innocuous, in the eye in which the disinfected contact lens is placed. Without wishing to limit the present invention to any particular theory of operation, it is believed that the scavenger component interacts with the active chelating or complexing sites of the chelating component so that such interacted chelating component is ineffective to chelate or complex further.

Any suitable scavenger component may be employed, provided that it functions as described herein and has no substantial or significant detrimental effect on the contact lens treated by the present composition or on the eye in which the contact lens is worn. Preferably, the scavenger components are ophthalmically acceptable at the concentrations present in the present compositions. Examples of particularly useful scavenger components are alkaline earth metal salts, more preferably alkaline earth metal inorganic salts, and mixtures thereof, such as calcium salts, magnesium salts and mixtures thereof. Very good results are obtained using a scavenger component selected from calcium chloride, magnesium chloride and mixtures thereof.

The amount or concentration of the scavenger component in the present compositions can vary widely and depends on various factors, for example, the specific scavenger component being employed, the specific chelating component and concentration thereof present in the disinfectant-containing composition and the like factors. Preferably, the concentration of the scavenger component is in the range of about 0.01 to about 0.5 or about 1% of the present composition.

The compositions of the invention can also include one or more additional components effective to provide at least one beneficial property to the compositions, the contact lens treated and/or the eye in which the contact lens is placed. These additional components preferably are ophthalmically acceptable and can be chosen from materials which are conventionally employed in the contact lens care compositions.

Acceptable effective concentrations for these additional components in the compositions of the invention are readily apparent to the skilled practitioner.

The aqueous liquid medium used is selected to have no substantial deleterious effect on the disinfected lens, or on the wearer of the disinfected lens. The liquid medium is constituted to permit, and even facilitate, the instant lens treatment or treatments. The aqueous liquid medium preferably includes an effective amount of a tonicity adjusting component to provide the liquid medium with the desired tonicity. The aqueous liquid medium of the present invention preferably includes a buffer component which is present in an amount effective to maintain the pH of the medium in the desired range. Such tonicity adjusting components and buffer components may be present in the aqueous liquid medium and/or may be introduced into the aqueous liquid medium. Among the suitable tonicity adjusting components that may be employed are those conventionally used in contact lens care products, such as various inorganic salts. Sodium chloride, potassium chloride, mannitol, dextrose, glycerin, propylene glycol and the like and mixtures thereof are very useful tonicity adjusting components. Among the suitable buffer components or buffering agents that may be employed are those conventionally used in contact lens car products. The buffer salts include alkali metal, alkaline earth metal and/or ammonium salts. Conventional organic buffers, such as Goode's buffers and the like, may also be employed. In addition, the aqueous liquid media may include one or more other materials, for example, as described elsewhere herein, in amounts effective to treat contact lens (for example, provide a beneficial property to the contact lens) contacted with such media.

Methods for enhancing the wearability of contact lenses are also included within the scope of the present invention. Such methods comprise contacting a contact lens, preferably a disinfected contact lens, on or in which is located a non-oxidative antimicrobial component with a liquid medium, preferably an aqueous liquid medium, containing an effective amount of an IC at conditions effective to inactivate the non-oxidative antimicrobial component located on or in the contact lens. The present compositions can be employed in accordance with the present methods.

The IC/contact lens contacting can occur in any convenient way provided that inactivation of the non-oxidative disinfectant component is obtained. For example, the contact lens can be contacted, e.g., manually rubbed, with one or more drops of the IC-containing composition for a time sufficient to provide for the inactivation of the non-oxidative antimicrobial component. In the event the contact lens is hydrophilic, such contacting preferably is continued for a period of time substantially equal to or at least about 70% as long as significant amounts of non-oxidative antimicrobial component are being desorbed from the lens.

Alternately, the contact lens containing on which the non-oxidative disinfectant component is located can be placed in the IC-containing composition for a period of time, on the order of about 10 seconds or about one minute or about ten minutes to about 30 minutes or about one hour or more to allow for the inactivation of the non-oxidative antimicrobial component. This contacting may be referred to as a rinse or a soak effective and preferably occurs at temperature conditions so that the aqueous liquid medium of the IC-containing composition is maintained substantially liquid, for example, in the range of about 10° C. to about 80° C. Ambient temperature is very effective.

In a particularly useful embodiment, the contact lens is contacted with a liquid material containing an effective disinfecting amount of a non-oxidative disinfectant component at conditions effective to disinfect the contact lens. After disinfection, the disinfected contact lens on or in which non-oxidative disinfectant component is located is contacted with a IC-containing composition, as described above.

In another embodiment, the contact lens is placed in the eye of a contact lens wearer directly after the contact lens is contacted with the IC-containing component composition, as described above. Preferably the carry over volume and residence time of the IC in the eye are such as to provide or maintain a concentration of IC as the non-oxidative antimicrobial component desorbs from the lens in the eye.

The liquid medium is preferably free of the non-oxidative antimicrobial component prior to the contacting step.

The following non-limiting examples illustrate certain aspects of the present invention.

EXAMPLE 1

A conventional soft hydrophilic contact lens (water content of about 60% by weight) is placed in about 2 ml of a commercially available multi-purpose contact lens solution sold by Bausch & Lomb under the trademark ReNu®. This solution is aqueous based and includes about 0.00005% (w/v) of polyaminopropyl biguanide as an antimicrobial agent and about 0.1%(w/v) of EDTA as a chelating agent. The hydrophilic contact lens is maintained in this solution at room temperature for about 8 to 12 hours. After this period of time the lens is disinfected.

The disinfected lens is removed from the solution.

The disinfected lens is rinsed in about 1 ml to 7 ml of a substantially isotonic aqueous solution including about 0.5% (w/v) of sodium carboxymethylcellulose and packaged in single or unit dosage increments without any preservative. This rinsing occurs for about 15 seconds, which is sufficient to allow the solution containing the carboxymethylcellulose to be sorbed, at least partially, in or on the contact lens. During this rinsing time, the carboxymethylcellulose interacts with the biguanide located on or in the contact lens to inactivate the biguanide.

After the rinsing step, the disinfected contact lens is placed directly in the eye of a human being. It is found that the human being experiences greater initial and overall comfort in wearing the lens relative to wearing a similarly disinfected lens which is not subjected to the above-noted rinsing step.

In addition, the wearer of the disinfected and rinsed contact lens is able to comfortably wear the lens for a longer period of time with reduced ocular stress, i.e. redness, staining, etc., relative to a similarly disinfected, but unrinsed lens. This enhanced performance may result from, in addition to the inactivation of the biguanide, elimination of other components in the disinfectant-containing composition, providing a physical barrier between the lens and the eye, and affecting surface cells of the eye to increase resistance to the biguanide.

EXAMPLE 2

The conventional and well known "slit lamp" test is conducted on both the disinfected (without rinsing) contact lens and the disinfected and rinsed contacts lens of Example 1. Results of these tests show reduced or lower slit lamp findings with the disinfected and rinsed contact lens. This advantageous result in because of the inactivation or deactivation of the biguanide during the rinsing step.

EXAMPLE 3

Example 1 is repeated except that the substantially isotonic aqueous solution includes about 0.03% to 0.05% (w/v) of calcium chloride. Substantially the same results as set forth in Example 1 are obtained. In addition, the calcium chloride is effective to fully complex the EDTA in the multi-purpose solution. Thus, contact lens wearers who may be sensitive to EDTA are provided with the additional benefit that this source of ocular sensitivity is reduced or even eliminated.

EXAMPLE 4

Example 1 is repeated except that after the disinfected lens is removed from the multi-purpose solution it is contacted with one or more drops (about 0.05 ml to about 0.2 ml) of the substantially isotonic aqueous solution identified in Example 1. The lens and drops of solution are manually rubbed together for about 15 seconds, which is sufficient to allow the solution containing the carboxymethylcellulose to be sorbed, at least partially, in or on the contact lens. During this rubbing, the carboxymethylcellulose interacts with the biguanide located on or in the contact lens to inactivate the biguanide.

After the rubbing, the disinfected contact lens is placed directly in the eye of a human being. It is found that the human being experiences greater initial and overall comfort in wearing the lens relative to wearing a similarly disinfected lens which is not subjected to the above-noted rubbing.

In addition, the wearer of the disinfected and rinsed contact lens is able to comfortably wear the lens for a longer period of time with reduced ocular stress, i.e., redness, staining, etc., relative to a similarly disinfected, but unrubbed lens. This enhanced performance may result from, in addition to the inactivation of the biguanide, elimination of other components in the disinfectant-containing composition, providing a physical barrier between the lens and the eye, and affecting surface cells of the eye to increase resistance to the biguanide.

EXAMPLE 5

Example 4 is repeated except that the substantially isotonic aqueous solution includes sufficient calcium chloride to fully complex the EDTA in the multi-purpose solution. Substantially the same results as set forth in Example 4 are obtained. In addition, the calcium chloride is effective to fully complex the EDTA in the multi-purpose solution. Thus, contact lens wearers who may be sensitive to EDTA are provided with the additional benefit that this source of ocular sensitivity is reduced or even eliminated.

EXAMPLE 6

Example 1 is repeated except that the substantially isotonic aqueous solution contains about 0.25% (w/v) of sodium carboxymethylcellulose, is packaged in a suitable multi-dose container, and includes a preservative. In addition, about 15 ml of this substantially isotonic solution is used. The preservative used in the solution is stabilized chlorine dioxide. This substantially isotonic solution contains about 0.003% (w/v) of stabilized chlorine dioxide and is buffered to a pH of between about 7.7 to 7.9.

Substantially the same results are obtained as in Example 1. In addition, it is found that the presence of the stabilized chlorine dioxide precursor has substantially no detrimental effect on the disinfected contact lens, on the wearing of the disinfected contact lens or on the eye of the contact lens wearer.

The use of such preservative is very beneficial. Thus, the ocular sensitivity resulting from the antimicrobial biguanide can be reduced or even eliminated without requiring that the IC, that is the sodium carboxymethyl cellulose, be present in an unpreserved, single dose form. The multi-dose or bulk IC-containing composition is less expensive to produce and can be more convenient than unit or single dose forms.

EXAMPLE 7

Example 6 is repeated except that the substantially isotonic aqueous solution includes about 0.03% to 0.05% (w/v) of calcium chloride. Substantially the same results as set forth in Example 6 are obtained. In addition, the calcium chloride is effective to fully complex the EDTA in the disinfected composition. Thus, contact lens wearers who may be sensitive to EDTA are provided with the additional benefit that this source of ocular sensitivity is reduced or even eliminated.

EXAMPLES 5 to 8 and 9

Examples 6 and 7 are repeated except that the disinfected lens is removed from the multi-purpose solution and placed in a conventional contact lens vial with about 10 ml of the preserved substantially isotonic aqueous solution. The lens is allowed to soak in this solution for about 8 hours.

Substantially the same results are obtained as in Examples 6 and 7, respectively.

EXAMPLES 10 to 18

Examples 1 to 9 are repeated except that the hydrophilic contact lenses are, over a period of about 2 weeks, disinfected a number of times using the multi-purpose solution. It is found that over this period of time the wearers of these contact lenses experience increasing ocular sensitivities to the wearing of these lenses. It is believed that over this period of time a build-up of the antimicrobial biguanide occurs in or on the lenses.

After a period of wear, the contact lenses are again subjected to contacting with the multi-purpose solution, resulting in the contact lenses being disinfected. The disinfected lenses are removed from the solutions. Each of the disinfected lenses is then contacted with the substantially isotonic aqueous solution as set forth in Examples 1 to 9, respectively.

Substantially the same results are obtained as in Examples 1 to 9, respectively. In addition, in each case the IC, that is the sodium carboxymethylcellulose, present in the substantially isotonic aqueous solution, is effective in inactivating the antimicrobial biguanide that builds-up on or in the contact lens after repeated disinfecting. Thus, depending on the individual lens wearer, the contact lens may be disinfected only once or more than once before contacting the lens with an IC-containing composition.

EXAMPLES 19 to 36

Examples 1 to 18 are repeated except that the substantially isotonic aqueous solution is free of sodium carboxymethylcellulose and includes an effective amount, in the range of about 0.1% to about 0.5%, (w/v), of sodium alginate.

Substantially the same results are obtained as in Examples 1 to 18, respectively.

The present examples make clear that the ocular sensitivity caused by non-oxidative antimicrobial components can be effectively and easily reduced, or even eliminated. The use of ICs, either in unpreserved or preserved compositions, effectively inactivates the antimicrobial component and enhances the wearability of the disinfected contact lens. Further, certain ICs can, because of their inherent viscosity and lubricity properties, further enhance lens wearability. The contact lens is preferably contacted with sufficient IC to inactivate all the non-oxidative antimicrobial component in or on the lens. If a relatively small volume, for example, less than about 5 ml or less than about 1 ml, of the IC-containing liquid medium is to be used per lens treatment, for example, in a single use or dose form, the concentration of the IC preferably is relatively high. Conversely, if a relatively large volume, for example, about 5 ml or more, of the IC-containing liquid medium is to be used per lens treatment, for example, in a multi-dose or bulk package, the concentration of the IC preferably is relatively low. Also, by choosing a preservative which results in little or no ocular sensitivity, the lens wearability advantages of the present invention can be obtained using cost effective and convenient multi-dose or bulk forms of IC-containing compositions. Moreover, a chelating agent scavenger can be used to provide additional contact lens wearability enhancements.

While this invention has been described with respect to various examples and embodiments, it is to be understood that the invention is not limited thereto, and that is can be variously practiced within the scope of the following claims.

What is claimed is:
1. A method for enhancing the wearability of a contact lens which comprises:
   contacting a contact lens on or in which is located a non-oxidative antimicrobial component selected from the group consisting of polycationic antimicrobial component and mixtures thereof with a liquid medium containing an amount in the range of about 5% (w/v) or less effective to inactivate substantially all the non-oxidative antimicrobial component located on or in said contact lens of an inactivating component selected from the group consisting of anionic cellulose derivatives, anionic acrylic acid-containing polymers, anionic methacrylic acid-containing polymers, anionic amino acid-containing polymers and mixtures thereof at conditions effective to inactivate said non-oxidative antimicrobial component located on or in said contact lens.
2. The method of claim 1 wherein said contacting comprises rubbing said contact lens with said liquid medium or rinsing said contact lens with said liquid medium or soaking said contact lens in said liquid medium.
3. The method of claim 1 which further comprises, prior to said contacting with said inactivating component, contacting said contact lens with a liquid material containing an effective disinfecting amount of said non-oxidative antimicrobial component at conditions effective to disinfect said contact lens.
4. The method of claim 1 wherein said inactivating component is selected from the group consisting of carboxymethylcelluloses and mixtures thereof.
5. The method of claim 1 wherein said non-oxidative antimicrobial component is selected from the group consisting of hexamethylene biguanide polymers and mixtures thereof.
6. A composition for enhancing the wearability of a contact lens which comprises:
   an aqueous liquid medium;
   an inactivating component soluble in said aqueous liquid medium, selected from the group consisting of anionic cellulose derivatives, anionic acrylic acid-containing polymers, anionic methacrylic acid-containing polymers, anionic amino acid-containing polymers and mixtures thereof and present in an amount in the range of about 5% (w/v) or less effective to inactivate substantially all of a non-oxidative, polycationic antimicrobial component located on or in a contact lens contacted with said composition; and
   a preservative component selected from the group consisting of per-salts, peroxides, alcohols, sorbic acid, chlorine dioxide precursors and mixtures thereof in an amount in a range of about 0.000001% to about 0.05% (w/v) effective to preserve said composition, the preserving activity of said preservative component being effective in the presence of said inactivating component, wherein said preservative component has a reduced propensity to cause discomfort in a human eye relative to the non-oxidative, polycationic antimicrobial component located on or in a contact lens contacted with said composition.
7. The composition of claim 6 wherein said inactivating component is selected from the group consisting of carboxymethylcelluloses, anionic acrylic acid-containing polymers, anionic methacrylic acid-containing polymers, anionic amino acid-containing polymers and mixtures thereof.
8. The composition of claim 6 wherein said inactivating component is selected from the group consisting of carboxymethylcelluloses and mixtures thereof.

9. The composition of claim 6 wherein said preservative component is selected from the group consisting of chlorine dioxide precursors and mixtures thereof.

10. The composition of claim 6 which further comprises a scavenger component present in an amount effective to inactivate a chelating component located on or in a contact lens contacted with said composition.

11. The composition of claim 10 wherein said scavenger component is ophthalmically acceptable and is selected from the group consisting of calcium salts, magnesium salts and mixtures thereof.

12. The method of claim 1 wherein said non-oxidative antimicrobial component is selected from the group consisting of poly quaternary ammonium salts, hexamethylene biguanide polymers and mixtures thereof.

* * * * *